United States Patent
McNab et al.

(10) Patent No.: US 10,324,057 B2
(45) Date of Patent: Jun. 18, 2019

(54) DETECTION APPARATUS AND METHOD FOR A FLEXIBLE PIPE

(71) Applicant: GE Oil & Gas UK Ltd, Nailsea, Bristol (GB)

(72) Inventors: John Cross McNab, Newcastle-upon-Tyne (GB); Geoffrey Stephen Graham, Newcastle-upon-Tyne (GB); Philip Michael Hunter Nott, Newcastle-upon-Tyne (GB); Phillip Edward Harley, Newcastle-upon-Tyne (GB); William James Shepherd, Newcastle-upon-Tyne (GB)

(73) Assignee: GE Oil & Gas UK Limited, Nailsea, Bristol (GB)

( * ) Notice: Subject to any disclaimer, the term of this patent is extended or adjusted under 35 U.S.C. 154(b) by 170 days.

(21) Appl. No.: 15/311,999

(22) PCT Filed: Mar. 25, 2015

(86) PCT No.: PCT/GB2015/050891
§ 371 (c)(1),
(2) Date: Nov. 17, 2016

(87) PCT Pub. No.: WO2015/177499
PCT Pub. Date: Nov. 26, 2015

(65) Prior Publication Data
US 2017/0122894 A1 May 4, 2017

(30) Foreign Application Priority Data
May 21, 2014 (GB) .................................. 1409036.9

(51) Int. Cl.
*G01N 27/24* (2006.01)
*G01N 27/02* (2006.01)
(Continued)

(52) U.S. Cl.
CPC .............. *G01N 27/24* (2013.01); *G01M 3/18* (2013.01); *G01N 17/02* (2013.01); *G01N 27/02* (2013.01)

(58) Field of Classification Search
CPC ........ G01N 17/02; G01N 22/00; G01N 22/04; G01N 27/02; G01N 27/24; G01N 27/902;
(Continued)

(56) References Cited

U.S. PATENT DOCUMENTS 3,526,831 A 9/1970 Smith
4,099,117 A * 7/1978 Erath ................... G01N 27/205
324/357

(Continued)

FOREIGN PATENT DOCUMENTS

EP 2706338 A1 3/2014
JP H0518849 A 1/1993
(Continued)

OTHER PUBLICATIONS

Search Report from the United Kingdom Intellectual Property Office for corresponding United Kingdom Patent Application No. GB1409036.9, dated Nov. 13, 2014, 4 pages.
(Continued)

*Primary Examiner* — Vinh P Nguyen
(74) *Attorney, Agent, or Firm* — Klarquist Sparkman, LLP

(57) ABSTRACT

A detection apparatus and method arranged to detect defects within a flexible pipe at least partially surrounded by seawater. The detection apparatus comprises a seawater electrode, an impedance monitor and a processor. The seawater electrode is arranged to be in contact with seawater surrounding at least part of a flexible pipe. The impedance monitor is arranged to measure the impedance between a metallic structural component of the flexible pipe extending
(Continued)

at least partially along the length of the flexible pipe and the seawater electrode in response to an electrical test signal applied to the seawater electrode. The processor is arranged to determine the distance from the seawater electrode to a pipe defect electrically connecting the metallic structural component to seawater using the measured impedance.

6 Claims, 15 Drawing Sheets

(51) Int. Cl.
 G01N 17/02 (2006.01)
 G01M 3/18 (2006.01)
(58) Field of Classification Search
 CPC ............... G01R 1/06772; G01R 29/0878; G01R 31/00; G01R 31/021; G01R 31/025; G01R 31/08; G01R 31/083; G01R 31/12; G01R 33/03; G01R 33/26; G01R 33/032; G01V 3/00; G01V 3/088; G01V 3/101; G01V 3/14; G01V 3/24; G01M 3/18
 See application file for complete search history.

(56) References Cited

U.S. PATENT DOCUMENTS

| 4,584,521 A | 4/1986 | Gaud et al. |
| 5,184,083 A | 2/1993 | Groover |
| 2008/0284441 A1* | 11/2008 | Kowalczyk ............ G01V 3/104 324/334 |
| 2009/0115433 A1 | 5/2009 | Bier |
| 2010/0289773 A1* | 11/2010 | Lin ....................... G06F 3/0428 345/175 |

FOREIGN PATENT DOCUMENTS

| WO | WO2007/042277 A1 | 4/2007 |
| WO | WO2008/083409 A1 | 7/2008 |
| WO | WO2013/093068 A1 | 6/2013 |

OTHER PUBLICATIONS

Search Report from the United Kingdom Intellectual Property Office for corresponding United Kingdom Patent Application No. GB1409036.9, dated Nov. 27, 2014, 2 pages.

International Search Report and Written Opinion of the International Searching Authority, dated Jun. 18, 2015, for corresponding International Application No. PCT/GB2015/050891, 17 pages.

First Office Action and Search Report (including English translation) from National Intellectual Property Administration, People's Republic of China, for Chinese Patent Application No. 2015800265005, dated Oct. 9, 2018, 32 pages.

"Non-Destructive Inspection and Estimation of Composite Materials," (including English translation), Chinese Society of Aeronautics and Astronautics, Jan. 31, 1997, 3 pages.

* cited by examiner

DETECTION APPARATUS AND METHOD FOR A FLEXIBLE PIPE

The present invention relates to a detection apparatus and method. In particular, the present invention relates to a detection apparatus arranged to detect defects within a flexible pipe, and a method of detecting defects within a flexible pipe. Particular embodiments relate to a detection apparatus suitable for detecting a pipe defect within an existing flexible pipe installation.

Traditionally flexible pipe is utilised to transport production fluids, such as oil and/or gas and/or water, from one location to another. Flexible pipe is particularly useful in connecting a sub-sea location (which may be deep underwater, say 1000 m or more) to a sea level location. The pipe may have an internal diameter of typically up to around 0.6 m. Flexible pipe is generally formed as an assembly of a flexible pipe body and one or more end fittings. The pipe body is typically formed as a combination of layered materials that form a pressure-containing conduit. The pipe structure allows large deflections without causing bending stresses that impair the pipe's functionality over its lifetime. The pipe body is generally built up as a combined structure including metallic and polymer layers.

In many known flexible pipe designs the pipe body includes one or more pressure armour layers. The primary load on such layers is formed from radial forces. Pressure armour layers often have a specific cross section profile to interlock so as to be able to maintain and absorb radial forces resulting from outer or inner pressure on the pipe. The cross sectional profile of the wound wires which thus prevent the pipe from collapsing or bursting as a result of pressure are sometimes called pressure-resistant profiles. When pressure armour layers are formed from helically wound wire forming hoop components, the radial forces from outer or inner pressure on the pipe cause the hoop components to expand or contract, putting a tensile load on the wires.

In many known flexible pipe designs the pipe body includes one or more tensile armour layers. The primary loading on such a tensile armour layer is tension. In high pressure applications, such as in deep and ultra-deep water environments, the tensile armour layer experiences high tension loads from a combination of the internal pressure end cap load and the self-supported weight of the flexible pipe. This can cause failure in the flexible pipe since such conditions are experienced over prolonged periods of time.

Unbonded flexible pipe has been used for deep water (less than 3,300 feet (1,005.84 m)) and ultra-deep water (greater than 3,300 feet) developments. It is the increasing demand for oil which is causing exploration to occur at greater and greater depths where environmental factors are more extreme. For example, in such deep and ultra-deep water environments, ocean floor temperature increases the risk of production fluids cooling to a temperature that may lead to pipe blockage. Increased depths also increase the pressure associated with the environment in which the flexible pipe must operate. As a result the need for high levels of performance from the layers of the flexible pipe body is increased. Flexible pipe may also be used for shallow water applications (for example less than around 500 m depth) or even for shore (overland) applications.

One way to improve the load response and thus performance of armour layers is to manufacture the layers from thicker and stronger and thus more robust materials. For example, for pressure armour layers in which the layers are often formed from wound wires with adjacent windings in the layer interlocking, manufacturing the wires from thicker material results in the strength increasing appropriately. However, as more material is used, the weight of the flexible pipe increases. Ultimately the weight of the flexible pipe can become a limiting factor in using flexible pipe. Additionally manufacturing flexible pipe using thicker and thicker material increases material costs appreciably, which is also a disadvantage.

Regardless of measures taken to improve the performance of armour layers within a pipe body, there remains a risk of defects arising within a flexible pipe. A defect may comprise damage to an outer wall of a flexible pipe body resulting in the ingress of seawater into an annulus within the pipe body such that seawater fills voids between the armour layer wires and other structural elements of the pipe. Armour layer wires and other structural elements are typically manufactured from steel or other metallic materials, which are vulnerable to accelerated corrosion upon contact with seawater. If such a defect is not detected promptly then the structural integrity of the pipe body can be compromised. Detection of defects has previously often required visual inspection of the pipe body, which can be hazardous, particular for deep water and ultra-deep water installations.

Certain embodiments of the invention provide the advantage that a defect within a pipe body can be detected without requiring periodic visual inspection. Defects can then be repaired, or the pipe body replaced. Detectable defects include a breach of the outer wall of a flexible pipe and the ingress of seawater into a pipe body annulus. Certain embodiments of the invention allow the location of a defect to be determined, with sufficient accuracy to allow a repair to be effected. Certain embodiments of the invention allow a defect to be located for an existing pipe body installation. That is, the detection apparatus is not reliant on having been installed or coupled to the pipe body in advance of a defect occurring and the detection apparatus can be used with existing pipe body designs that are already widely deployed.

According to a first aspect of the present invention there is provided a detection apparatus arranged to detect defects within a flexible pipe at least partially surrounded by seawater, the detection apparatus comprising: a seawater electrode arranged to be in contact with seawater surrounding at least part of a flexible pipe; an impedance monitor arranged to measure the impedance between a metallic structural component of the flexible pipe extending at least partially along the length of the flexible pipe and the seawater electrode in response to an electrical test signal applied to the seawater electrode; and a processor arranged to determine the distance from the seawater electrode to a pipe defect electrically connecting the metallic structural component to seawater using the measured impedance.

The seawater electrode may be arranged to move relative to the flexible pipe, the impedance monitor is arranged to measure the impedance between the metallic structural component and the seawater electrode at two or more positions and the processor is arranged to determine the distance from the seawater electrode to the pipe defect for each position and to triangulate the location of the pipe defect.

The seawater electrode may be arranged to be lowered through the seawater surrounding the flexible pipe or the seawater electrode is coupled to a steering mechanism such that the location of the seawater electrode relative to the flexible pipe can be controlled.

The detection apparatus may further comprise two or more spaced apart seawater electrodes separately coupled to the impedance monitor; wherein the impedance monitor is arranged to measure the impedance between the metallic structural component and each seawater electrode and the processor is arranged to determine the distance from each seawater electrode to the pipe defect and to triangulate the location of the pipe defect.

The detection apparatus may further comprise a position locator coupled to the seawater electrode and arranged to provide an indication of the location of the seawater electrode relative to the flexible pipe; wherein the processor is arranged to determine the location of the pipe defect from the measured impedance and the position of the seawater electrode.

The seawater electrode may comprise a loop arranged to pass around the flexible pipe, the loop incorporating two or more conducting elements spaced around the flexible pipe, the conducting elements being arranged to be coupled together and connected to the impedance monitor or separately connected to the impedance monitor.

The processor may be further arranged to determine the location of the pipe defect using a three dimensional model of the location of the flexible pipe.

The impedance monitor may be arranged to measure the impedance for test signal applied to the seawater electrode at a first frequency selected according to the distance between the seawater electrode and the flexible pipe.

The impedance monitor may be arranged to measure the impedance for two or more test signal frequencies applied to the seawater electrode, and the processor is arranged to determine the distance from the seawater electrode to a pipe defect by comparison of the measured impedances at the first and second frequencies.

The impedance monitor may be arranged to apply electrical test signals to the seawater electrode at a plurality of frequencies between 10 Hz and 100 kHz.

According to a second aspect of the present invention there is provided a method of detecting defects within a flexible pipe at least partially surrounded by seawater, the method comprising: immersing a seawater electrode into seawater surrounding at least part of a flexible pipe; coupling an impedance monitor between a metallic structural component of the flexible pipe extending at least partially along the length of the flexible pipe and the seawater electrode; generating an electrical test signal and applying the electrical test signal to the seawater electrode; measuring the impedance between the metallic structural component and the seawater electrode in response to the test signal; and determining the distance from the seawater electrode to a pipe defect electrically connecting the metallic structural component to seawater using the measured impedance.

The method may further comprise: moving the seawater electrode relative to the flexible pipe; measuring the impedance between the metallic structural component and the seawater electrode at two or more positions; determining the distance from the seawater electrode to the pipe defect for each position; and triangulating the location of the pipe defect.

The method may further comprise: immersing two or more spaced apart seawater electrodes into seawater surrounding at least part of the flexible pipe, each seawater electrode being separately coupled to the impedance monitor; measuring the impedance between the metallic structural component and each seawater electrode; determining the distance from each seawater electrode to the pipe defect; and triangulating the location of the pipe defect.

According to a third aspect of the present invention there is provided a detection apparatus arranged to detect defects within a flexible pipe at least partially surrounded by seawater, the detection apparatus comprising: a seawater electrode in contact with seawater surrounding at least part of a flexible pipe and arranged to generate an electric field within the seawater relative to the potential of a metallic structural component of the flexible pipe extending at least partially along the length of the flexible pipe; and an electric field probe arranged to measure an electric field vector within the seawater surrounding the flexible pipe; wherein the measured electric field vector is indicative of the direction from the electric field probe to a pipe defect electrically connecting the metallic structural component to seawater.

The detection apparatus may further comprise: a position locator 1416 (FIG. 14) coupled to the electric field probe and arranged to provide an indication of the location of the electric field probe relative to the flexible pipe; and a processor arranged to determine the location of the pipe defect from the measured electric field vector and the position of the electric field probe.

The seawater electrode may be arranged to generate an electric field at a first frequency, and the processor is arranged to synchronise the measured electric field vector to the first frequency to determine the location of the pipe defect.

The electric field probe may be arranged to move relative to the flexible pipe and the processor is arranged to triangulate the location of the pipe defect from electric field vectors measured at two or more positions of the electric field probe.

The electric field probe may be arranged to be lowered through the seawater surrounding the flexible pipe or the electric field probe is coupled to a steering mechanism such that the location of the seawater electrode relative to the flexible pipe can be controlled.

The processor may be further arranged to determine the location of the pipe defect using a three dimensional model of the location of the flexible pipe.

The detection apparatus may further comprise: an orientation sensor 1418 (FIG. 14) coupled to the electric field probe and arranged to determine the three dimensional orientation of the electric field probe; wherein the electric field probe is arranged to measure a three dimensional electric field vector.

According to a fourth aspect of the present invention there is provided a method of detecting defects within a flexible pipe at least partially surrounded by seawater, the method comprising: immersing a seawater electrode into seawater surrounding at least part of a flexible pipe; generating an electric field using the seawater electrode within the seawater relative to the potential of a metallic structural component of the flexible pipe extending at least partially along the length of the flexible pipe; and measuring an electric field vector within the seawater surrounding the flexible pipe; wherein the measured electric field vector is indicative of the direction from the electric field probe to a pipe defect electrically connecting the metallic structural component to seawater.

The method may further comprise: determining the location of the electric field probe relative to the flexible pipe; and determining the location of the pipe defect from the measured electric field vector and the position of the electric field probe.

The method may further comprise: moving the electric field probe relative to the flexible pipe; and triangulating the location of the pipe defect from electric field vectors measured at two or more positions of the electric field probe.

Advantageously, the detection apparatus allows a pipe body defect such as a breach in an outer seawater resistant layer to be detected and located for an existing flexible pipe installation. That is, the detection apparatus may be used once a defect such as a breach is suspected, and so the detection apparatus may be referred to as a post event breach location apparatus.

Embodiments of the invention are further described hereinafter with reference to the accompanying drawings, in which.

In the drawings like reference numerals refer to like parts.

Figure 1:
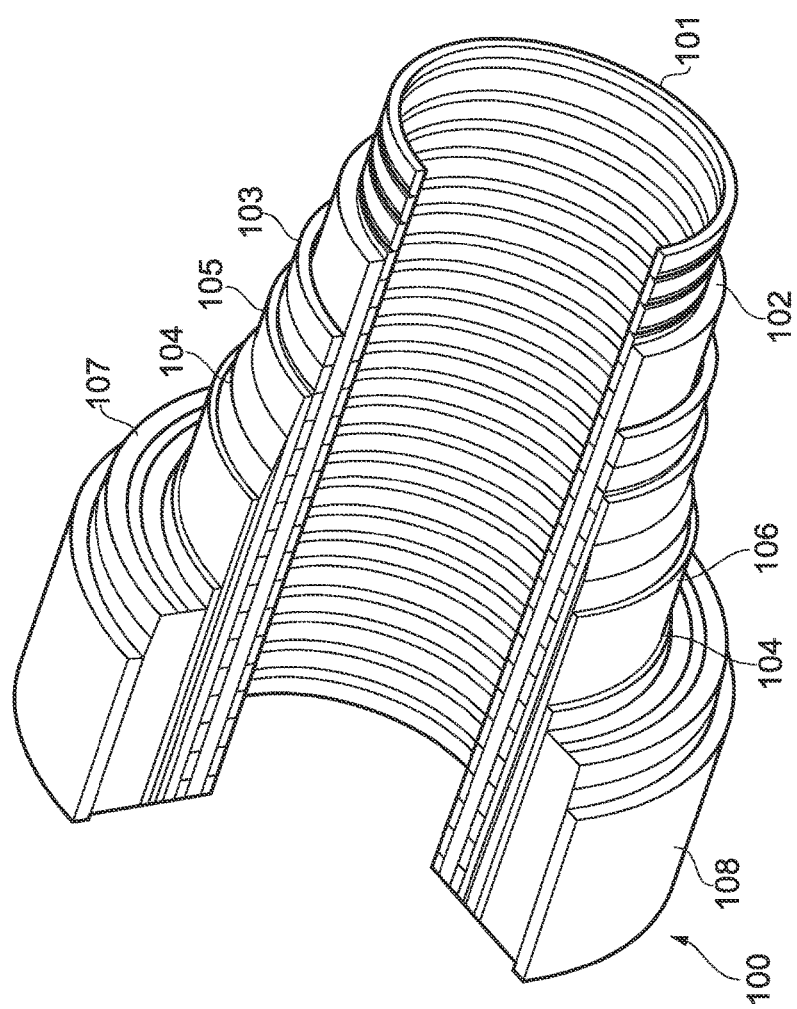
FIG. 1 illustrates a flexible pipe body.

Throughout this description, reference will be made to a flexible pipe. It will be understood that a flexible pipe is an assembly of a portion of a pipe body and one or more end fittings in each of which a respective end of the pipe body is terminated. FIG. 1 illustrates how pipe body 100 is formed in accordance with an embodiment of the present invention from a combination of layered materials that form a pressure-containing conduit. Although a number of particular layers are illustrated in FIG. 1, it is to be understood that the present invention is broadly applicable to coaxial pipe body structures including two or more layers manufactured from a variety of possible materials. It is to be further noted that the layer thicknesses are shown for illustrative purposes only.

As illustrated in FIG. 1, a pipe body includes an optional innermost carcass layer 101. The carcass provides an interlocked construction that can be used as the innermost layer to prevent, totally or partially, collapse of an internal pressure sheath 102 due to pipe decompression, external pressure, and tensile armour pressure and mechanical crushing loads. It will be appreciated that certain embodiments of the present invention are applicable to 'smooth bore' operations (i.e. without a carcass) as well as such 'rough bore' applications (with a carcass).

The internal pressure sheath 102 acts as a fluid retaining layer and comprises a polymer layer that ensures internal fluid integrity. It is to be understood that this layer may itself comprise a number of sub-layers. It will be appreciated that when the optional carcass layer is utilised the internal pressure sheath is often referred to by those skilled in the art as a barrier layer. In operation without such a carcass (so-called smooth bore operation) the internal pressure sheath may be referred to as a liner.

An optional pressure armour layer 103 is a structural layer with a lay angle close to 90° that increases the resistance of the flexible pipe to internal and external pressure and mechanical crushing loads. The layer also structurally supports the internal pressure sheath, and typically consists of an interlocked construction.

The flexible pipe body also includes an optional first tensile armour layer 105 and optional second tensile armour layer 106. Each tensile armour layer is a structural layer with a lay angle typically between 10° and 55°. Each layer is used to sustain tensile loads and internal pressure. The tensile armour layers are often counter-wound in pairs.

The flexible pipe body shown also includes optional layers of tape 104 which help contain underlying layers and to some extent prevent abrasion between adjacent layers.

The flexible pipe body also typically includes optional layers of insulation 107 and an outer sheath 108, which comprises a polymer layer used to protect the pipe against penetration of seawater and other external environments, corrosion, abrasion and mechanical damage.

Each flexible pipe comprises at least one portion, sometimes referred to as a segment or section of pipe body 100 together with an end fitting located at one end or both ends of the flexible pipe. An end fitting provides a mechanical device which forms the transition between the flexible pipe body and a connector. The different pipe layers as shown, for example, in FIG. 1 are terminated in the end fitting in such a way as to transfer the load between the flexible pipe and the connector.

Figure 2:
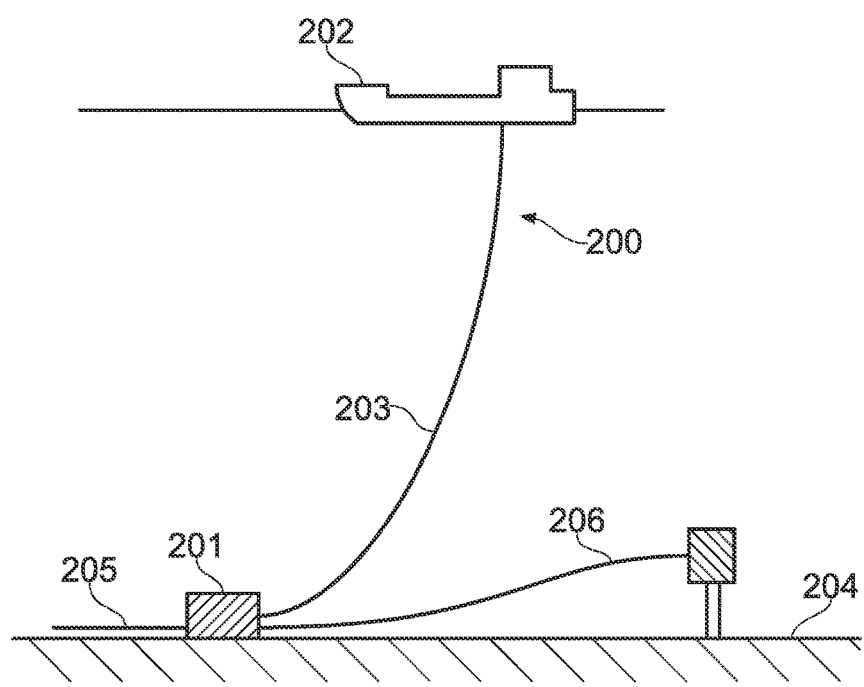
FIG. 2 illustrates a riser assembly incorporating a flexible pipe body.

FIG. 2 illustrates a riser assembly 200 suitable for transporting production fluid such as oil and/or gas and/or water from a sub-sea location 201 to a floating facility 202. For example, in FIG. 2 the sub-sea location 201 includes a sub-sea flow line 205. The flexible flow line 205 comprises a flexible pipe, wholly or in part, resting on the sea floor 204 or buried below the sea floor and used in a static application. The floating facility may be provided by a platform and/or buoy or, as illustrated in FIG. 2, a ship. The riser assembly 200 is provided as a flexible riser, that is to say a flexible pipe 203 connecting the ship to the sea floor installation. The flexible pipe may be in segments of flexible pipe body with connecting end fittings. FIG. 2 also illustrates how portions of flexible pipe can be utilised as a flow line 205 or jumper 206. It will be appreciated that there are different types of riser, as is well-known by those skilled in the art. Embodiments of the present invention may be used with any type of riser, such as a freely suspended (free, catenary riser), a riser restrained to some extent (buoys, chains), totally restrained riser or enclosed in a tube (I or J tubes).

As noted above, defects in a flexible pipe body can compromise the structural integrity of the pipe body. In particular, a breach or rupture of an outer seawater resistant layer can allow seawater ingress into the pipe body annulus between an innermost barrier layer and the outer seawater resistant layer. With reference to FIG. 1 the outer seawater resistant layer may comprise the polymer outer sheath 108 and the innermost barrier layer may comprise the internal pressure sheath 102. The pipe body annulus is occupied by metallic structural components such as the tensile armour layers 105, 106 of FIG. 1. Such components are frequently formed from steel or other metals and are susceptible to rapid corrosion in the presence of seawater. There will now be described detection apparatuses and methods which can detect a breach of an outer resistant layer of a flexible pipe body.

Figure 3:
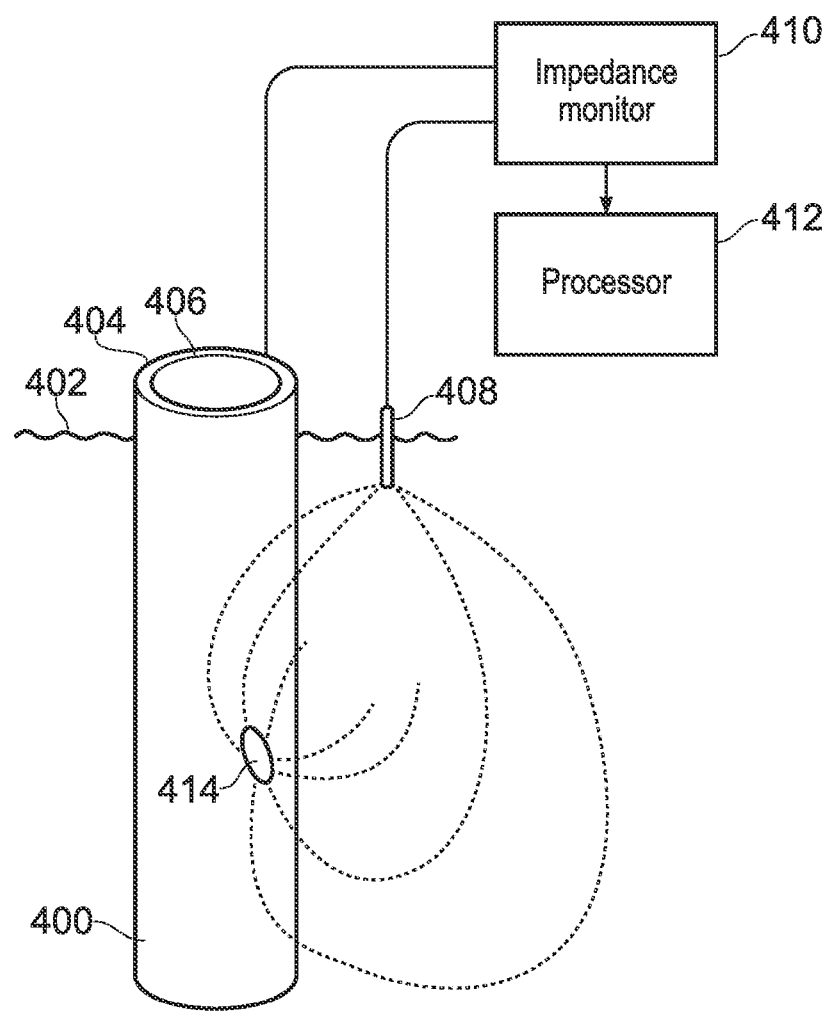
FIG. 3 illustrates a detection apparatus in accordance with an embodiment of the invention.

FIG. 3 illustrates a detection apparatus coupled to a flexible pipe body in accordance with an embodiment of the present invention. The detection apparatus is arranged to detect a change to a flexible pipe body which may indicate a defect (and in particular a breach allowing seawater or other fluids into the pipe body annulus). The detection apparatus may be coupled to a warning system arranged to provide an output signal to an operator of the flexible pipe alerting the operator to potential damage to the pipe. The output signal may, for instance, be a visual or audible alarm.

As discussed above, a flexible pipe body may be constructed from at least one layer of polymer barrier, including an outer seawater resistant layer 304 and at least one layer of co-axial metallic structural elements 306, 308. The metallic structural elements, for instance the tensile armour layers 105, 106 of FIG. 1, are designed to satisfy purely mechanical properties of the structure of the pipe body. However, they are electrically conductive and this property is exploited in accordance with certain embodiments of the present invention. Detection apparatuses in accordance with certain embodiments of the invention are arranged to be used to detect the location of a breach within a flexible pipe with at least one metallic layer or structural component. As will be described in greater detail below, the detection apparatus is arranged so that it can be used to detect the location of a breach of an existing flexible pipe installation and so no modification of the pipe body is required.

It will be appreciated that in the event of a breach of an outer seawater resistant layer the pipe body annulus will begin to fill with seawater. Metallic structural components within the pipe body annulus thus come into electrical contact with the seawater surrounding the pipe body, and so a change in impedance between the seawater surrounding the pipe body and the metallic structure of the pipe body will result. A detection apparatus in accordance with certain embodiments of the invention is arranged to measure the impedance between the metallic structural components of a pipe body and a seawater electrode, from which it can be deduced whether there is a breach and the approximate location of the breach. The skilled person will understand that measuring the impedance between these two points is directly equivalent to measuring the conductivity of the seawater between these two points.

As will be described below, the detection apparatus illustrated in FIG. 3 couples to an electrically conductive structural component extending at least partially along the length of a pipe body. Metallic structural components with flexible pipes are typically electrically coupled together at an end fitting and the end fitting in turn is coupled to the local Earth upon the production platform to reduce the risk of explosion. The detection apparatus is coupled to the local Earth upon the production platform, and thereby indirectly coupled to the metallic structural components of the pipe body. The electrically conductive member may comprise a metallic structural component such as a single tensile armour wire or a tensile armour wire layer.

The outer seawater resistant layer of a flexible pipe body may be manufactured from a polymer material with known, intrinsic electrical insulation properties. Seawater has known electrical conduction properties, though this may vary from location to location, for instance due to variation in the salinity of the seawater, and so a detection apparatus in accordance with an embodiment of the invention may require calibration before use to adapt to local conditions. A physical breach in the form of an aperture in the outer seawater resistant layer of a flexible pipe permits a conductive path between the seawater and the steel internal structure of the pipe body. In accordance with certain embodiments of the present invention an electrical impedance measurement made between seawater surrounding a flexible pipe and the internal metallic structure of the pipe body provides a means of indicating the presence of a breach. Specifically, in the event that the measured impedance is below a certain threshold, it can be inferred that a breach has occurred and seawater is in contact with the internal metallic structure of the pipe body.

Referring in detail to FIG. 3, this shows a flexible pipe body 400, which as discussed above may comprise a riser. The pipe body is at least partially surrounded by seawater, schematically illustrated by the pipe body 400 extending below the surface level 402 of the sea. As discussed above, such a flexible pipe body is constructed from multiple layers of polymer barrier, including an outer seawater resistant layer 404 and at least one layer of metallic structural elements 406, for instance the tensile armour layers 105, 106 of FIG. 1. A seawater electrode 408 is in contact with seawater in proximity to the pipe body 400. As will be described in greater detail below in connection with FIGS. 7 to 10, the location of the seawater electrode 408 may be varied in order to ascertain the location of a breach to a greater accuracy, or alternatively multiple seawater electrodes 408 may be provided to allow the triangulation of the location of a breach. Each seawater electrode 408 may alternatively be referred to as a probe or a conductivity probe.

An impedance monitor 410 is coupled to the seawater electrode 408 and to a metallic structural component 406 of the pipe body 400 via the local Earth upon the production platform. The impedance monitor 410 provides a measurement of the impedance between the seawater electrode 408 and the pipe body 400 (alternatively, this can be considered to be a conductivity measurement). The impedance measurement is supplied to a processor 412 for analysis. If the measured impedance is less than a threshold when the seawater electrode is proximate to the pipe body then this may indicate that there is a breach. For instance, a very high impedance measurement could indicate that there is no breach. The impedance of a polymer barrier layer is approximately 1 MΩ. However, the approximate impedance of seawater is 5 Ω and so a low measured impedance may indicate that seawater has penetrated the pipe body annulus through a breach. As discussed in greater detail below care must be taken to ensure that the measured impedance is not that of the seawater between the seawater electrode and the hull of the production vessel which typically forms the local Earth. In one embodiment the impedance monitor 412 is arranged to measure impedance in the range of 0-10 kΩ. An impedance above 10 kΩ is registered as the maximum 10 kΩ due to the measurement system saturating at that value. Advantageously, this accurately records the absence of a polymer barrier layer while allowing greater measurement resolution at lower impedance values. If there is any seawater conductivity path between the structure of the pipe body and the seawater electrode (when the seawater electrode is relatively close to the location of a breach) the measured impedance is well below 10 kΩ. The processor 412 is arranged to provide an appropriate output signal to an operator of the flexible pipe alerting the operator to potential damage to the pipe.

Unlike the predominantly electron flow conduction in metals, the electrical conduction in seawater is dependent on ion mobility, and this leads to significant variation in observed conductivity with the frequency of the applied measurement excitation. This is shown schematically in the FIG. 4 which shows relative attenuation of an applied alternating current signal at various low frequencies and between electrodes spaced at 10 m, 100 m, and 1 Km. Certain embodiments of the present invention takes advantage of the attenuation data of FIG. 4 by applying frequency agile excitation of the impedance monitor 410. Measurement of the impedance at a single excitation frequency can give an indication of the distance through the seawater between the seawater electrode 408 and the breach. Certain embodiments of the invention take advantage of this by moving the seawater electrode between different locations relative to the pipe body to increase the measurement accuracy by triangulating the results. However, as noted above, due to the variation in seawater conduction, additionally or alternatively the impedance monitor may be excited at two or more frequencies allowing the results to be compared, and from that information an approximate location of the breach determined. In certain embodiments the excitation frequency of the impedance monitor is in the range 10 Hz to 1 kHz. In other embodiments the maximum excitation frequency of the impedance monitor may be 100 kHz. It will be appreciated by the skilled person that the detection system of FIG. 3 could also operate using DC test signals to determine whether there is a pipe defect through detected seawater conduction to the seawater electrode. However, it will be understood that this would not allow the detection of the location of the defect.

Figure 5:
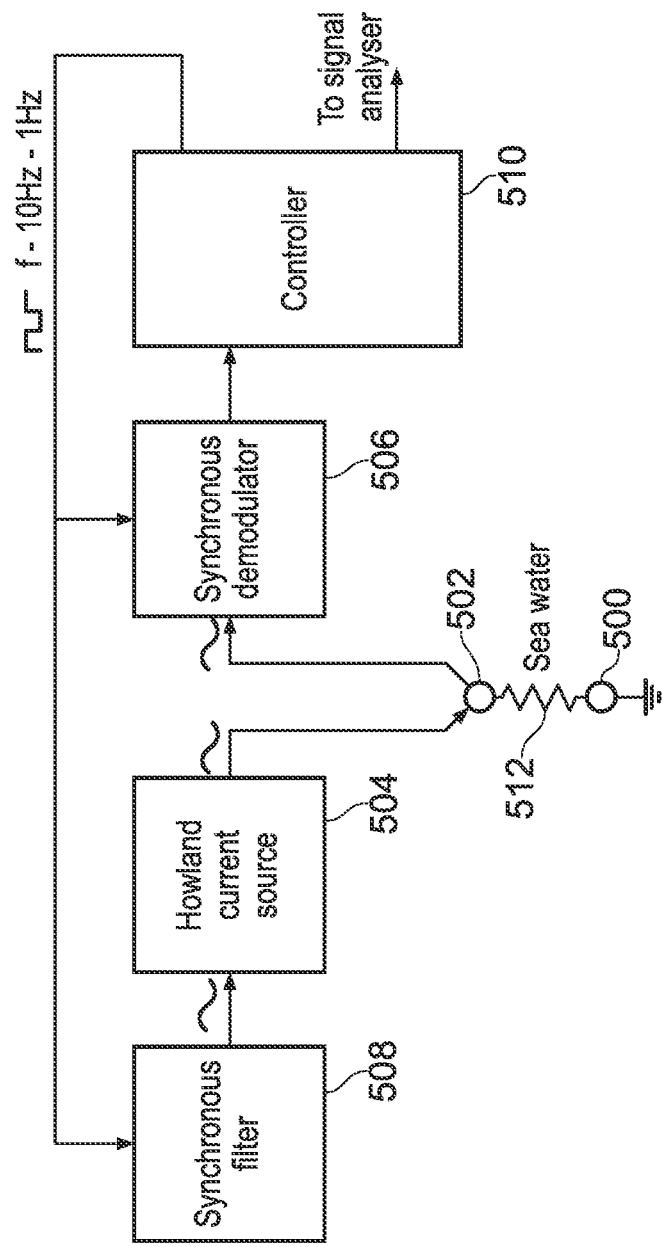
FIG. 5 illustrates an impedance monitor forming part of the detection apparatus of FIG. 5.

One embodiment of the impedance monitor is shown in greater detail in FIG. 5. A first electrode 500 is coupled to the local Earth upon the production platform (and hence connected to the metallic structural components of the pipe body) and a second electrode 502 is coupled to the seawater electrode. The second electrode 502 is coupled between a Howland current source 504 and a synchronous demodulator 506. The impedance monitor may operate in either a voltage or current source mode. In FIG. 5 a Howland current source 504 is used as it provides a good linearity of response. The Howland current source 504 is shown connected to the second electrode. The Howland current source 504 thus supplies a current to the seawater electrode in response to an input signal supplied by a synchronous filter 508. The seawater electrode thus energises the seawater surrounding the pipe body generating an electric field extending between the seawater electrode and the production platform and any breach within the pipe body outer seawater resistant layer (as will be explained in greater detail below in connection with FIG. 13). The current may be AC current. In one embodiment, preferably the signal may be a sinusoidal waveform AC current. Other waveforms, for instance a square wave could be used, however sinusoidal is preferred because then there are no harmonics present, which could interfere with the operation of the frequency dependent range measurement system. That is, the applied electrical test signal may be AC. In other embodiments a voltage source may be used. The synchronous filter 508 provides a signal under the control of a pulsed control signal from controller 510, which additionally supplies the same control signal to the synchronous demodulator 506. The synchronous demodulator 506 is arranged to analyse the voltage generated across the seawater between the seawater electrode and the Earth of the production vessel at each frequency. The synchronous demodulator 506 supplies an output signal to the controller 510, which is indicative of the voltage of the second electrode 502 relative to Earth. In the event of a breach of the polymer barrier, the voltage of the second electrode 502 is dependent upon the applied current and the seawater impedance between the electrodes 500, 502 indicated by resistor symbol 512. This may only be the case if the seawater electrode is positioned relatively close to the location of the breach, and so certain embodiments of the present invention allow for the location of the seawater electrode to be varied in order to ensure that the conduction between the seawater electrode and the breach is not swamped by the conduction between the seawater electrode and the production platform. The controller 510 is arranged to generate an output signal indicative of the impedance between the electrodes 500, 502 by comparison of the supplied current and the measured voltage. The output signal is provided to the processor 412, which is arranged to determine whether a breach is detected.

Figure 4:
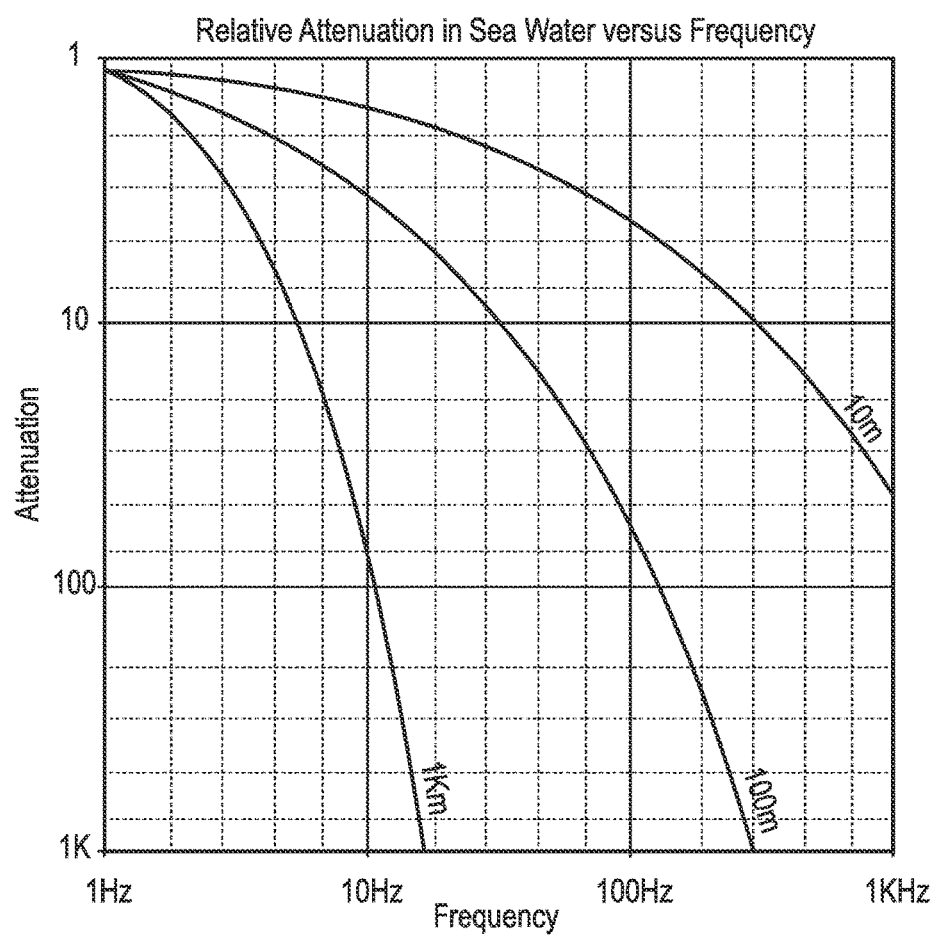
FIG. 4 is a graph illustrating the attenuation of an electrical signal relative to the frequency of the signal for three different distances.

In accordance with certain embodiments of the present invention the processor 412 is arranged to instruct the impedance monitor to perform impedance measurements at a range of excitation frequencies (for instance 10 Hz, 30 Hz, 100 Hz, 300 Hz and 1 kHz), which by cross reference to the graph of FIG. 4 (or by reference to a look up table within the processor 412) allow an estimation of the position of a breach to be determined. The accuracy of this computation is dependent on a number of factors including the size of the breach, the salinity and temperature of the seawater, the attitude of the pipe body (e.g. vertical to horizontal) and the electrical conductivity of the steel inner structure.

Figure 6:
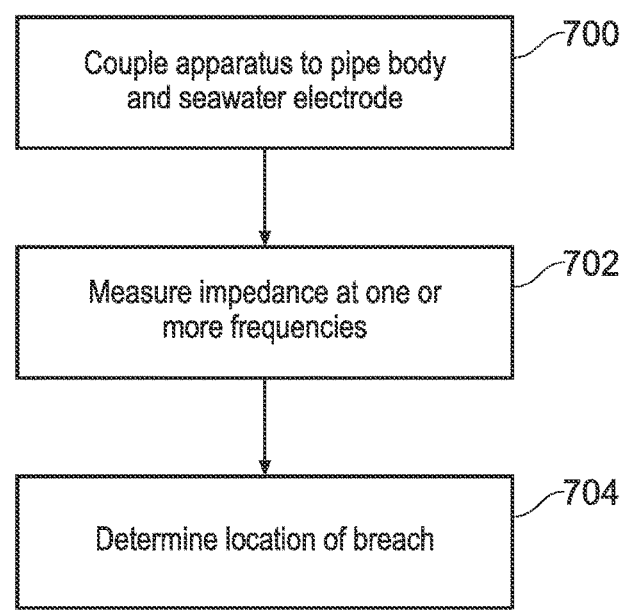
FIG. 6 is a flow chart illustrating a detection method in accordance with the embodiment of FIG. 2.

Referring now to the flow chart of FIG. 6, a detection method in accordance with the present invention will now be described. At step 700 the detection apparatus illustrated in FIG. 3 is coupled to an electrically conductive member within the pipe body (via the Earth upon the production platform) and to a seawater electrode. At step 702 the impedance between the electrodes is measured for at least one first frequency. At step 704 the frequency and impedance data is used to determine the location of a breach.

Advantageously, embodiments of the present invention described above do not interfere with active cathodic protection systems coupled to pipe bodies owing to the fact that no excitation signal is applied to the metallic structural components of the pipe body.

In accordance with certain embodiments of the invention the seawater electrode (also referred to as a seawater conductivity probe) is energised with at least one frequency or a low swept or switched frequency to measure the return Earth path through a breach to the metallic structural components of the pipe body (which in turn are connected to Earth). In order to accurately locate a breach requires knowledge of the location of the probe relative to the pipe body and the inferred distance from the seawater electrode to the breach (as described above). Advantageously, if the distance to the breach can be determined from multiple locations then triangulation may be used to provide a more accurate determination of the breach location. Measurements from multiple locations can be achieved either by moving the probe or by providing multiple probes. The seawater conductivity probe may use a swept low-frequency signal. Preferably, a series of readings are taken around the riser along its length. Triangulation indicates a breach location. Conductivity data is typically transmitted back to the surface and collated for analysis. Conductivity measurements (including the frequency used and signal strength) can be overlaid on a data indicating the probe location to build a 3D model of conductivity. When overlaid on a 3D model of the subsea pipes a breach location can be identified.

Figure 7:
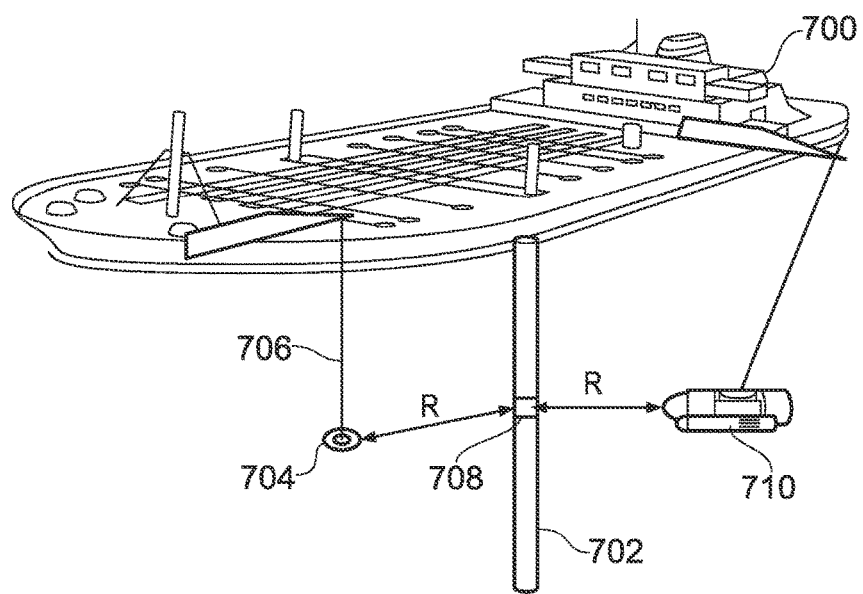
FIGS. 7 to 9 illustrates possible deployment scenarios for a detection apparatus in accordance with certain embodiments of the present invention.

Referring now to FIG. 7 this illustrates two possible deployment approaches for a probe. FIG. 7 shows a production platform 700 (a vessel) and a flexible pipe 702 extending downwards from the production vessel 700 and surrounded by seawater. The first approach is to dip the probe 704 over the side of the production platform attached to a cable 706. This probe reads the seawater conductance from the probe to the breach 708 marked R. This drawing is a simplification of the principle as the vessels hull acts as an additional (and large) return path to Earth. Depending upon the location of the breach 708 this background path may render it impossible to locate the breach. The basic probe approach is capable of detecting the breach location to approximately 100 m or better depending upon how close the cable 706 runs relative to the pipe 702. The depth of the probe may be indicated by the length of cable paid out. Conductivity measurements may be performed at multiple depths, with the depth having the largest conductance measured being likely to indicate the depth of the breach along the length of the pipe 702. Used like this without steering of the probe, the detection apparatus may be used for initial survey work. The cable 706 is preferably combined with communications and power supply cables for controlling the probe. The probe 704 may be dipped over the side of the vessel 700 at multiple locations around the pipe 702 to increase the measurement accuracy.

Once the dipping probe has given an approximate breach location (or in place of performing dipping measurements) a probe coupled to a Remotely Operated Vehicle 710 (ROV) may be used to steer the location of the probe close to the location of a suspected breach. As an alternative to using an ROV, any other means for actively steering the position of the probe may be used. The ROV 710 may be coupled to the production vessel 700 by an umbilical 712, which also serves to supply power and communications to the probe as for the dipping probe 704. The ROV's position is tracked using a 3D sonar position system which can be used to map out the background return paths to allow a better prediction of the breach location. Implementation also requires a subsea chart of deployed production equipment.

The ROV needs to be unearthed while in the water to not generate its own return path. Operating a probe coupled to an ROV may allow the breach location to be detected to an accuracy of approximately 20 m or better.

Figure 8:
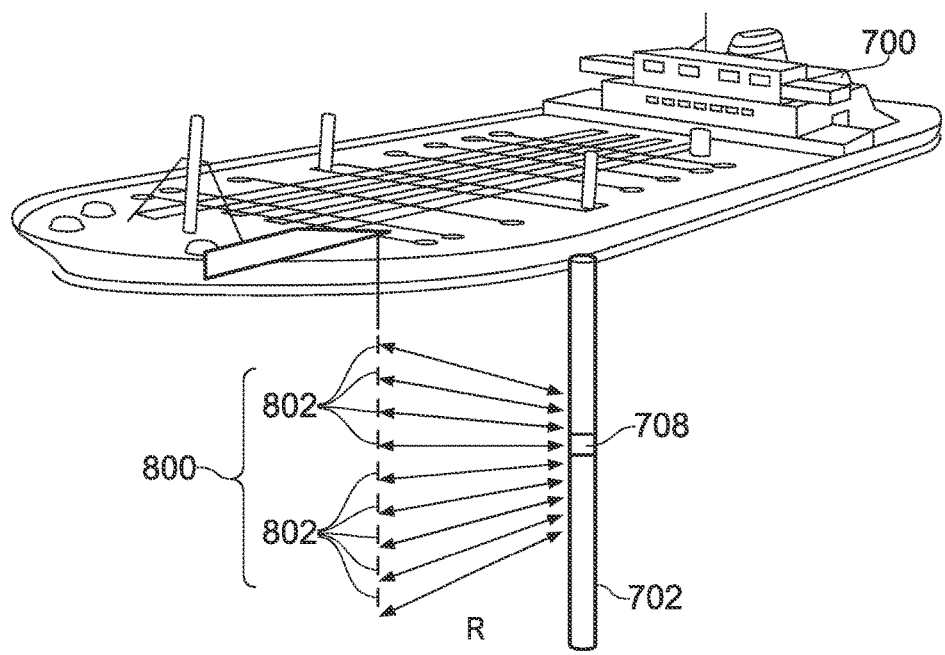

Referring now to FIG. 8, in accordance with a further embodiment an array of probes may be provided. For instance, the array may be provided in the form of a towed array cable 800 which has multiple individual conductors 802 positioned axially along a cable. The deployment of the towed array cable 800 is generally the same as for the dipping probe 704 and cable 706 shown in FIG. 7. The towed array cable 800 can be positioned next to the pipe 702 and each conductor 802 can be multiplexed to read the conductivity at each point along the cable 800. Advantageously, this embodiment allows the measurement of the distance to the breach from multiple locations (multiple depths below the surface of the sea) without requiring that the cable is moved. This allows for the rapid collection of data to aid possible ROV deployment.

Figure 9:
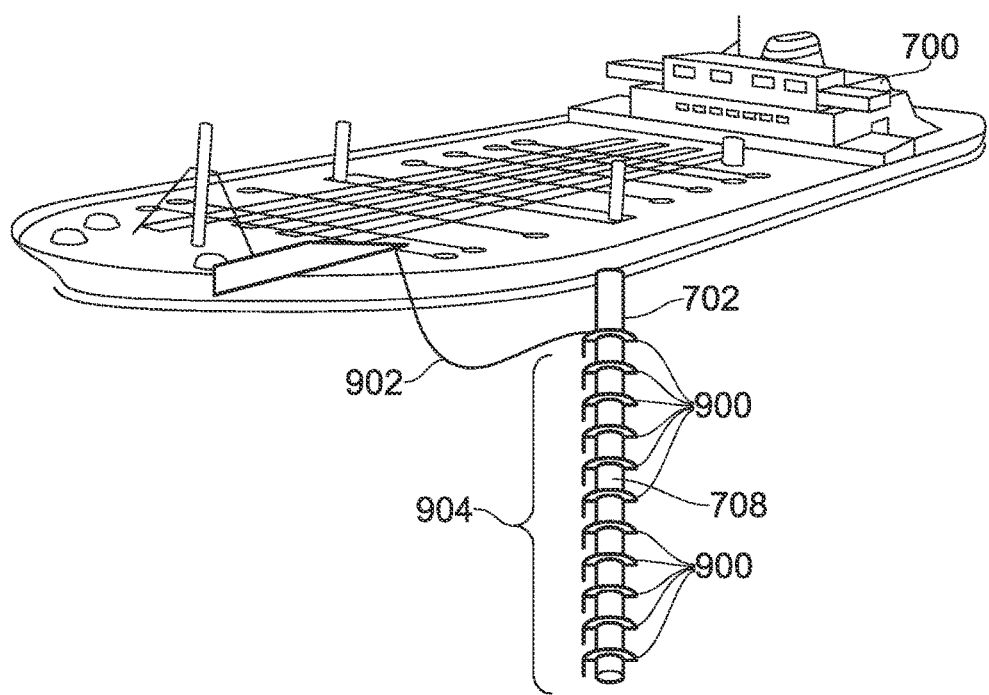

Referring now to FIG. 9, in accordance with a further embodiment one or more conductive hoops 900 may be placed around the outside of the pipe 702. Each hoop may comprise either a single conducting element or multiple conducting elements spaced around the circumference of the pipe 702. If multiple conducting elements are provided spaced apart around the circumference of the pipe 702 then the orientation of a breach around the circumference of the pipe 702 may be established. Each conductive hoop 900 is coupled to a cable 902 running up to the vessel 700 for communications and power, as for the embodiments of FIGS. 7 and 8. If a single hoop 900 is used the hoop 900 can be lowered and readings taken to locate the breach. If a single conducting element is used, this method gives a 360 degree return path and due to its locality with a breach an accurate location is provided. A hoop array 904 formed from multiple hoops 900 may be deployed by sliding along the pipe 702. Alternatively, a hoop array 904 may be preinstalled by positioning the hoops along the pipe 702 or incorporating the hoops 900 into the pipe or components such as joints and buoyancy.

Figure 10:
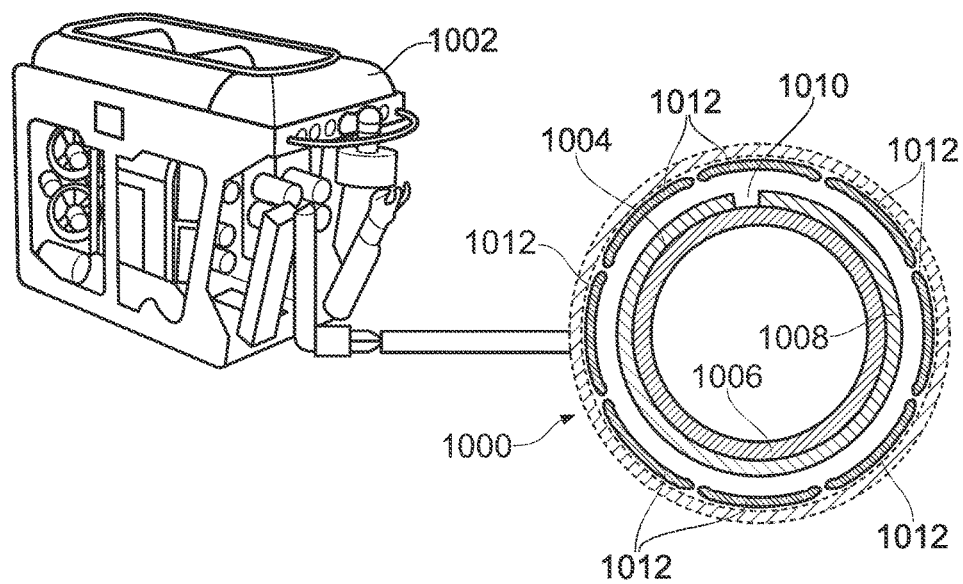
FIG. 10 illustrates a detection apparatus sensor suitable for mounting upon an ROV in accordance with an embodiment of the present invention.

Referring now to FIG. 10, in accordance with a further embodiment, a clamp 1000 may be attached to an ROV 1002 and arranged to be coupled around a pipe 1004 (shown in cross section). For instance, the clamp 1000 may include a hinged portion (not shown) arranged to open to admit the pipe 1004. The pipe 1004 shows a metallic structural layer 1006 and an outer seawater resistant layer 1008 in which a breach 1010 is formed. The clamp 1000 includes multiple conductors 1012 which may be separately energised so that the orientation of the breach about the circumference of the pipe 1004 may be ascertained. A clamp 1000 coupled to an ROV 1002 may thus be used to locate and map a breach both along the risers length and circumference. The conductors 1012 may initially be connected together to form a ring to detect the breach axially along the pipe 1004. Once the breach area is detected the conductors 1012 may be individually scanned to locate the breach position on the circumference of the pipe 1004. This method could also be used to measure the extent of a breach, for instance the circumferential size and axial length of a slit in the outer seawater resistant layer 1008. This method greatly reduces the vessels Earth return background interference due to the probe being placed in close proximity to the pipe.

As noted above, owing to the fact that the conductivity of seawater is variable, for a particular deployment location it may be desirable to calibrate the detection apparatus. For instance, this calibration may be achieved by attaching a metal plate to a pipe. The metal plate is connected to the Earth of the production vessel via an insulated wire, such that the metal plate simulates a breach at a known location.

Figure 11:
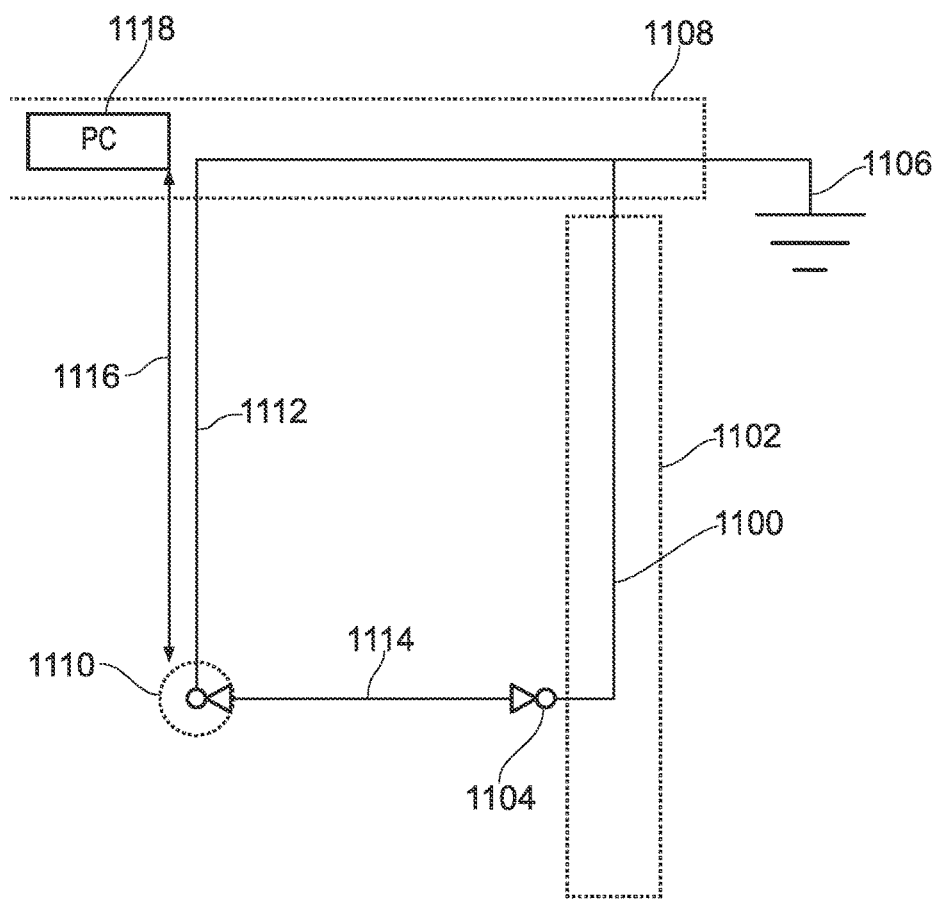
FIG. 11 is an electrical schematic for a detection apparatus in accordance with an embodiment of the present invention.

As noted above, existing pipe installations do not readily allow for energising the metalwork within the pipe in a manner to create a signal that can be remotely detected. This is due to the fact that metallic components are electrically connected together through the pipe end-fitting, which is itself bonded to the zero volts potential (Earth) on board the production platform. As discussed above, the present invention instead relies upon a seawater conductivity probe to energise the seawater surrounding the pipe, which completes a circuit through a breach in the riser coating to the metal work of the pipe body. Referring now to FIG. 11 this is an electrical schematic illustrating the measured conductivity path. Metallic structural components 1100 within the pipe 1102 are exposed to the surrounding seawater through a breach 1104 in the outer seawater resistant layer of the pipe body. The metallic structural components 1100 are electrically coupled to a top side end fitting (not shown) and then on to the zero volts potential (Earth) 1106 on board the production platform 1108. A seawater conductivity probe 1110 is positioned proximate to the pipe 1102 (via a cable or ROV as discussed above), and the probe 1110 is coupled by wire 1112 to Earth 1106. The probe 1110 is energised, for instance using the impedance monitor of FIG. 5 (not shown) in order to provide a measure of the conductance (or, equivalently, the impedance) of the seawater path 1114 between the probe 1110 and the breach 1104. FIG. 11 further shows a communications cable 1116 extending between the probe 1110 and a PC 1118 (or equivalent data analysis and collation equipment) on board the production platform 1108. While data collation could be performed within the probe 1110 for later analysis or real time analysis at the probe 1110, it is preferable that data is returned to the relative security of the production platform 1108.

Figure 12:
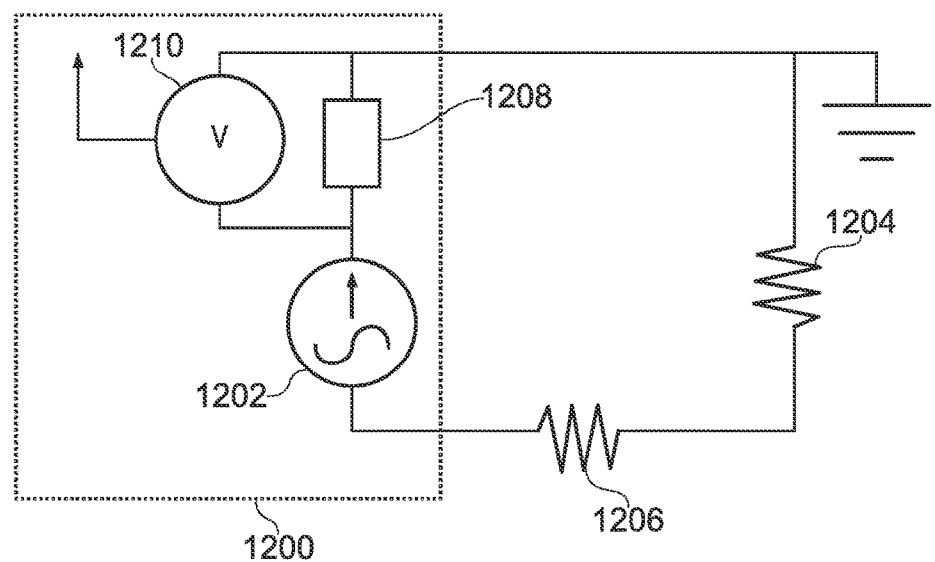
FIG. 12 is a circuit diagram for a detection apparatus in accordance with an embodiment of the present invention.

Referring now to FIG. 12, this illustrates a simplified electrical circuit of a detection apparatus 1200 in use in accordance with an embodiment of the present invention. A low frequency constant current source 1202 may be used to determine the total circuit conductivity, on the assumption that the internal resistance 1204 of the pipe body and the production platform remains unchanged. In practice, the internal resistance 1204 may vary according to how far along the pipe the breach is, though this internal resistance is relatively small compared to the seawater resistance 1206 in the event of a breach and so may be measured or modelled before a breach occurs and assumed to remain constant. The current source 1202 is used to energise the circuit such that the seawater resistance 1206 can be measured with reference to the voltage across a standard resistor 1208 using a voltmeter 1210.

Figure 13:
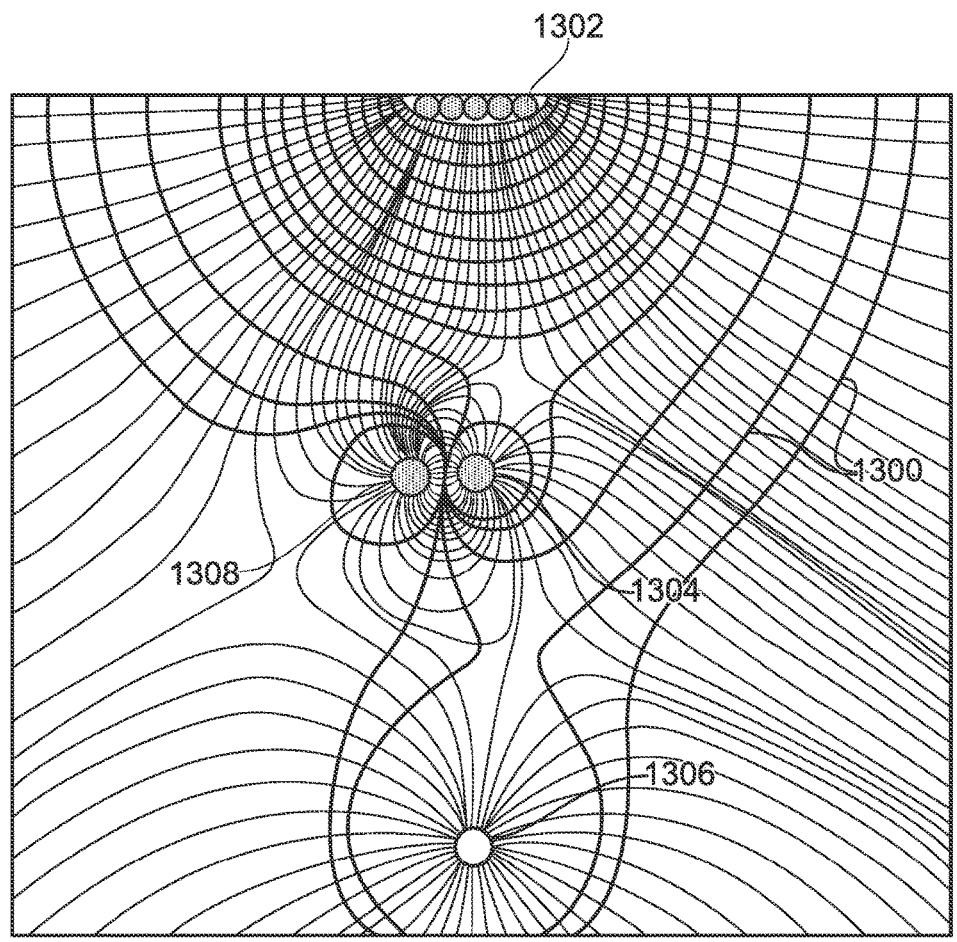
FIG. 13 is a modelled electric field diagram illustrating the effect of a seawater riser with a mid-way breach upon the electric field when operating a detection apparatus in accordance with an embodiment of the present invention.

As discussed above, given that the resistance of seawater varies with frequency (as shown in FIG. 4) driving the constant current source 1202 with different frequencies allows the system to effectively provide different ranges of operation. This may advantageously be used by operating at a relatively low frequency when the probe is remote from the pipe. Alternatively, higher frequency ranges allow discrimination of breach locations over shorter distances, and so allows very large alternative current paths that are not of interest (in particular through the hull of the production platform) to be filtered out to reveal the small localised return path through the breach. The need to discriminate return paths can be clearly seen by reference to FIG. 13 which shows a modelled electrical field (indicated by equipotential field lines 1300. FIG. 13 shows a model of a production platform hull 1302, a breach 1304 part way along a pipe (not shown) and the pipe bottom 1306 at which point the metallic structure of the pipe body is typically again exposed to the seawater by connection to an aluminium anode for cathodic protection. The hull 1302, breach 1304 and pipe bottom 1306 are all at the same potential (the zero volts, Earth, of the production platform). A probe 1308 is shown relatively close to the breach 1304 and field lines 1310 are shown coupling the probe 1310 to each of the hull 1302, breach 1304 and pipe bottom 1306. It can be seen that the hull 1302 forms a significant return path and so has a significant effect on the apparent conductivity of the seawater. To avoid this, for possible breach locations close to the ship, higher frequencies may be used with the probe close to the pipe (for instance, less than 10 m). Further down the pipe, a lower frequency can be used further from the pipe body (for instance, 100 m) to allow for more rapid scanning for breaches. The effect of the ship's hull and the bottom end-fitting is to create dead zones where it may be difficult or impossible to locate a breach, even with the use of higher frequencies. This effect will be largest for the ship's hull due to its sheer size.

As discussed above, analysis using two different frequencies is desirable. By operating the probe at several distinct alternating frequencies with known differing conductivities in seawater the location of a breach may be more accurately determined. However, it will be appreciated that embodiments of the present invention may locate a breach using only a single frequency, with increased accuracy achieved by moving the probe closer to the suspected location of the breach and/or performing triangulation using several measurements taken from different locations. Phase sensitive conductivity/impedance measurement allows for more sensitive detection.

In accordance with an alternative embodiment of the present invention, in place of measuring the impedance between a mobile probe and the breach as described above, an electric field may be established between a static probe and the breach. A second mobile probe may then measure the electric field surrounding the pipe in all three planes at known positions. This way, the electric field pattern resulting from the static probe energising the seawater can be examined for both magnitude and direction. An electric field vector measured relatively close to the location of a breach may indicate the location of the breach. Phase sensitive detection allows the polarity of the detected field to be determined, such that the vector may directly point to the location of the breach.

Figure 14:
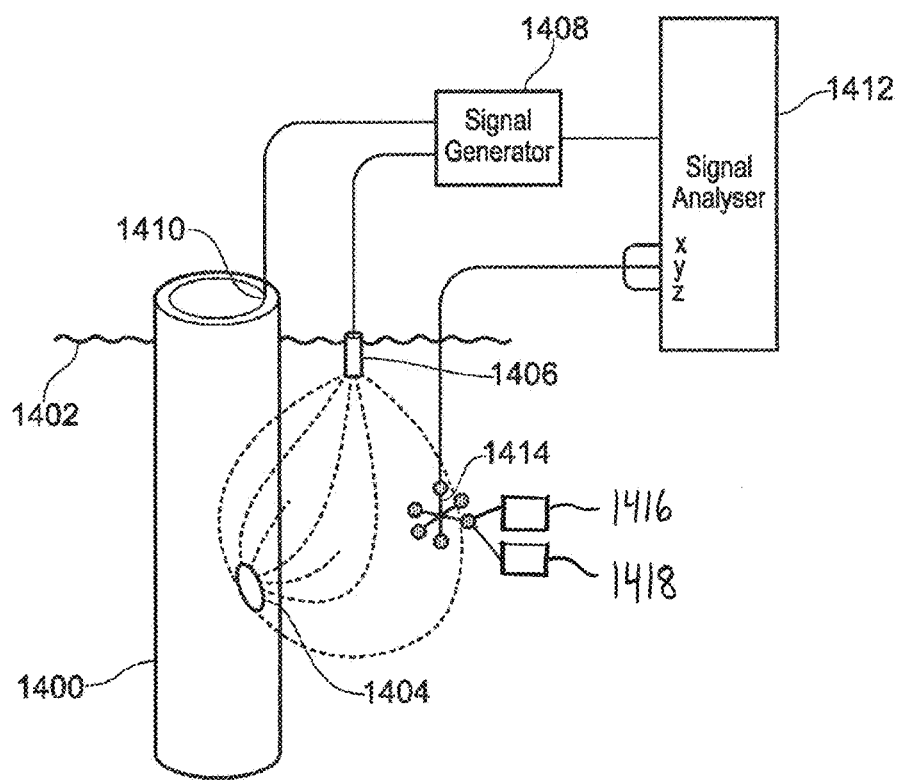
FIG. 14 illustrates a detection apparatus in accordance with another embodiment of the invention.

Referring to FIG. 14, this illustrates a detection apparatus in accordance with this alternative embodiment of the invention. Pipe 1400 is shown extending underneath the surface of the sea 1402 and pipe 1400 has a breach 1404. A static seawater electrode 1406 is energised by signal generator 1408 which is also coupled to the metallic structure 1410 of the pipe body via the local Earth of the production platform (not shown). The static electrode 1406 is energised using a constant voltage source to establish an electric field in the seawater surrounding the pipe 1400. This differs from the constant current source described in previous embodiments used to perform conductivity/impedance measurements. A signal analyser 1412 is coupled to the signal generator such that the measured electric field can be correlated to the phase of the signal supplied to the static electrode 1406 allowing the direction of an electric field vector to be established. A second probe 1414 is provided that can be moved relative to the pipe 1400, for instance by being attached to a cable and dipped into the sea or by being coupled to an ROV, as described above. The mobile probe 1414 is coupled to the signal analyser to provide an indication of the electric field measured in three dimensions. The location of the mobile probe may be directly determined using a 3D sonar transponder as described above.

This electric field vector approach offers considerable advantages over the above described techniques. Not only does it have a greater sensitivity, but also the vector allows the breach to be physically pointed to. This means that when deployed in the field, fewer measurement points need to be recorded. The mobile probe 1414 is mobile within a zone in the vicinity of the pipe 1400, but distant from the energising electrode 1406 to ensure that the measured vector does not simply point to the electrode 1406. The mobile probe 1414 may comprise three pairs of opposing electrodes spaced a small distance apart (for instance 0.5 m) apart, each oriented at right angles to the other to measure the electric field in three parallel planes. Three differential amplifiers within the sensor establish the electrode potential between each individual pair of electrodes, and from this information, the magnitude and direction (that is, the vector) of the electric field within the seawater at the point of measurement can be established. By moving the probe's position within the zone, and noting the vector values, the electric field vector pattern may be analysed to indicate the position of the breach with a degree of accuracy that typically surpasses that of the previously described embodiments. Interpretation of the results of the electric field measurement require knowledge of the position of the mobile probe, for instance using a sonar transponder as described above, and also the orientation of the probe, which may be established using gyroscopes, for instance MEMS based gyroscopes. An umbilical connecting the probe to the surface carries, as well as power, a reference signal at the delivered frequency, as this is required to allow the sign of the vector to be established.

Figure 15:
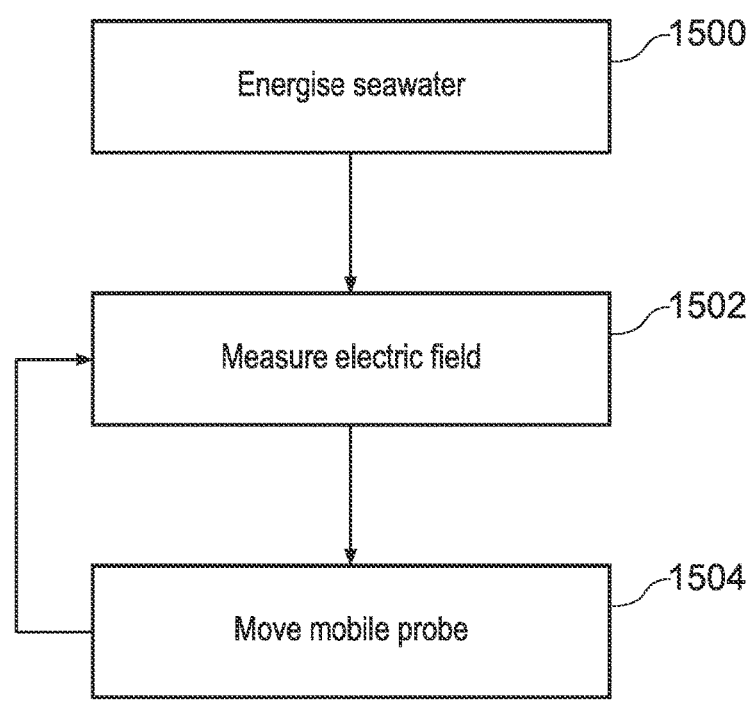
FIG. 15 is a flow chart illustrating a detection method in accordance with the embodiment of FIG. 14.

Referring now to FIG. 15 this is a flowchart illustrating a method of operating the detection apparatus of FIG. 14. At step 1500 the static electrode is deployed and used to establish a static electric field in the seawater surrounding a potential breach. At step 1502 the electric field is measured at a first point using the mobile probe in order to locate the breach. Depending upon the electric field vector measured at step 1502, the mobile probe is moved towards the suspected breach location at step 1504. This may be an iterative process in which the mobile probe is move progressively towards a potential breach until its probable location is determined to a sufficient degree of accuracy.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers or characteristics described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A detection apparatus arranged to detect defects within a flexible pipe at least partially surrounded by seawater, the detection apparatus comprising:
   a seawater electrode arranged to be positioned in contact with seawater surrounding at least part of a flexible pipe;
   a signal generator arranged to energize the seawater electrode to generate an electric field within the seawater relative to an electrical potential of a metallic structural component of the flexible pipe extending at least partially along the length of the flexible pipe;
   an electric field probe arranged to move relative to the flexible pipe and the seawater electrode and arranged to measure the electrical field in three dimensions to provide electric field vectors within the seawater surrounding the flexible pipe at two or more measurement positions of the electric field probe, wherein each measured electric field vector is indicative of the direction from the measurement position to a pipe defect electrically connecting the metallic structural component to seawater;
   a position locator coupled to the electric field probe and arranged to provide an indication of the location of the electric field probe relative to the flexible pipe at each measurement position of the electric field probe; and
   a processor arranged to triangulate the location of the pipe defect from the measured electric field vectors and the position of the electric field probe at each measurement position.

2. A detection apparatus according to claim 1, wherein the seawater electrode is arranged to generate an electric field at a first frequency, and the processor is arranged to synchronise the measured electric field vector to the first frequency to determine the location of the pipe defect.

3. A detection apparatus according to claim 1, wherein the electric field probe is arranged to be lowered through the seawater surrounding the flexible pipe or the electric field probe is coupled to a steering mechanism such that the location of the seawater electrode relative to the flexible pipe can be controlled.

4. A detection apparatus according to claim 1, wherein the processor is further arranged to determine the location of the pipe defect using a three dimensional model of the location of the flexible pipe.

5. A detection apparatus according to claim 1, further comprising:
   an orientation sensor coupled to the electric field probe and arranged to determine the three dimensional orientation of the electric field probe;
   wherein the electric field probe is arranged to measure a three dimensional electric field vector.

6. A method of detecting defects within a flexible pipe at least partially surrounded by seawater, the method comprising:
   immersing a seawater electrode into seawater surrounding at least part of a flexible pipe;
   energizing the seawater electrode with a signal generator to generate an electric field using the seawater electrode within the seawater relative to an electrical potential of a metallic structural component of the flexible pipe extending at least partially along the length of the flexible pipe;
   moving an electric field probe relative to the flexible pipe and the seawater electrode to measure the electrical field in three dimensions to provide electric field vectors within the seawater surrounding the flexible pipe at two or more measurement positions of the electric field probe, wherein each measured electric field vector is indicative of the direction from the measurement position to a pipe defect electrically connecting the metallic structural component to seawater;
   determining the location of the electric field probe relative to the flexible pipe at each measurement position of the electric field probe; and
   triangulating the location of the pipe defect from the measured electric field vectors and the position of the electric field probe at each measurement position.

* * * * *